United States Patent [19]

Salomon et al.

[11] Patent Number: 5,650,285
[45] Date of Patent: Jul. 22, 1997

[54] HUMAN CRIPTO-RELATED GENE AND METHOD OF MEASURING CR-3

[75] Inventors: David S. Salomon, Germantown, Md.; Maria G. Persica, Naples, Italy

[73] Assignee: The United States of America as represented by the Department of Health and Human Services, Washington, D.C.

[21] Appl. No.: 463,335

[22] Filed: Jun. 5, 1995

Related U.S. Application Data

[62] Division of Ser. No. 154,198, Nov. 17, 1993, which is a division of Ser. No. 749,001, Aug. 23, 1991, Pat. No. 5,264,557.

[51] Int. Cl.⁶ .................................................. G01N 33/53
[52] U.S. Cl. ................................... 435/7.1; 530/399
[58] Field of Search .......................... 530/399; 435/7.1

[56] References Cited

U.S. PATENT DOCUMENTS 5,256,643 10/1993 Perisco ............................... 514/12

OTHER PUBLICATIONS

Ciccodicola, A et al; "Molecular characterization of a gene of the 'EGF family' expressed in undifferentiated human NTERA2 teratocarcinoma cells.," The EMBO Journal, vol. 8, No. 7, pp. 1987–1991, (1989).

Dono, R. et al, Am. J. Human Genetics (USA) Sep. 1991, vol. 49, (3) pp. 555–565, "Isolation & Characterization of the CRIPTO Autosomal Gene and Its X–linked Related Sequence" (abstract).

Ciccodicola, Alfredo, et al. (1989) "Molecular characterization of a gene of the 'EGF family' expressed in undifferentiated human NTERA2 teratocarcinoma cells", The EMBO Journal, 8:1987–1991.

Dono, Rosanna, et al. (1991) "Isolation and Characerization of the CRIPTO Autosomal Gene and Its X–linked Related Sequence", Am. J. Hum. Genet, 49:555–565.

Wallace, R. Bruce, et al. (1987) "Oligonucleotide Probes for the Screening of Recombinant DNA Libraries", Methods in Enzymology, 152:432–442.

Primary Examiner—James C. Housel
Assistant Examiner—Ginny Allen Portner
Attorney, Agent, or Firm—Townsend & Townsend & Crew LLP

[57] ABSTRACT

The present invention relates, in general, to a human CRIPTO-related gene. In particular, the present invention relates to a DNA segment encoding a human CRIPTO-related gene; polypeptides encoded by said DNA segment; recombinant DNA molecules containing the DNA segment; cells containing the recombinant DNA molecule; a method of producing a human CRIPTO-related polypeptide; a DNA segment encoding a genomic clone of the human CRIPTO gene (CR-1); antibodies specific to CR-3; and a method of measuring the amount of CR-3 in a sample.

6 Claims, 13 Drawing Sheets

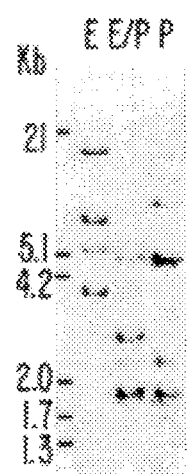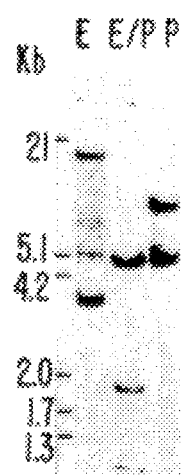 
FIG. IA.
FIG. IB.

CR-1  →  GCCGGCACTCCCACTGGAGAGTCCCCAGCTGCCTCTGGCCG|CCCCTCCCCTCTCCG|GGGCAC

CR-3  →  AAGCTTGCGCGCCATGTAAGGTAAAGTGACTGATTCTATAGCAATCCAATTGTTCCTTTGTCTGCCGTTTACATATAACAA
         CTGGCGCCCGCCGGTCCTCCGGGTTCCGCCCTGGAATTCGACTTCAAGTCTGGAGCCCCAAGGAACCCCTCCTGACCCTGA

TGTTGTCAATGTTTGATTGAAAATACCTAGCAGGTG
         ACTTCTATCTCCAGTTTCAAGCTTCCTAGTCTTCCCCACACACACACCTAGTCCTCCAGGCGGAGAGCA|CCCCTTTCT|TGGCCACCCGGGTATCC

T G AA A                              C
         CCCAGGGAGTACGGGGCTCAAAACACCCCTTTCTGAAAAACAAAGGTGGAAGCAAATTTCAGGAAGTAAACTTCTGAAATAAAATAAATATGA
                                                                                                G
                                A
         ATGCCCTGAGACCCATACATTTTCAGTTTTTCCTAATTAAAGCAATTACTTTCCACCACCCCTCCAACCTGAATCACCAACTGATTAGAGAAAC

TGA|TTTTTCTCTTTTTCTTTTTTTTCCC|GAAAAGAGTACCCTCGTGCAACTAATGATAGAGATATTAGGGCTAGTTAACCACAG

∆
         TTTTACAAGA|CTCCCTCTTCCC|GCGTGTGGGCCATTGTCATGCTGTGTCGGT|CCCGCC|CACCTGAAAGGTCTCC|CCGACTGGGGTTTGTTGTT
                                           CG                                  ↓↓                   A
         GAAGAAGGAGAATCCCCGGAAAGGCTGAGTCTCAAGGTCAAACGTCCAAGGCCCTCCAGTTTCCCCTGGACGCCCTGCTCCT
                  ∆                                                             T
         GCTTCTGCTAGACCCTTCTGGGGAAAACGAATTTCTCATTTCTTTAAATTGCCATTTTCGCTTTAGGAGAGATGAATGTTTCCTTGGCTGTTT
                                                           +1                                  V
         TGGCAATGACTCTGAATTAAAGCGATGCTAACGCCCTCTTTCCCCCTAATTGTTAAAAGCTATGACTGCAGGAAGATGGCCGCTTCTCTTACAG
                                                           M  D  C  R  K  M  A  R  F  S  Y  S

FIG. 2A.

IVS1
●---
GTATGAGCTAATCTTAGAATAGTGAACTTTTTTGATTGCTAGAGATTGCCAGCTTAGGAAGTAATGTTCTACACTGTCATTTGATTTTCTCCTT
GCTCAAGCCCTTAAAAGAGCTGCCAACCGACTGCTGTTTTCCTGAAAGACCTGGAATTTCACATGGTTACTTCTAACTTTGCCATTGGCTTTAAC
ATTTTCGTGTTAATGTTAATTTCATTTTATGTTAATGACTCTGCCTATGAAATAGTGTTTCTTACTTCTTGTACAAATAAAGGTCAGTACTACA
ACCAAATTTAAATCTTCCGAAAAGATTAAAGGTATAAGCAGATTCAATACTTGGCAAAACTATTAAGATAATAGCAAAAAAAAAAACCCAC
ATTTTTACCTAAAAACCTTTTAAGTGATTGGTTAAAATAGTTTGGCCGGTGCGGTGGCTCACGCCTGTAATCCTAGCACTTTGGGAGGCAGAGG
CGGGTGGATCACTGAGGTCAGGAGACCAGCCTGGCCAACATGGCAAAACCCCGTCTCTATTAAAAATACAAAAATTAGCCAAGCATGGTGGCGGC
ACCTGTAATCCCAGCTACTCTGGAGGCTGAGGCAGGAGAATTGCTTGAACTGGGAGGNCAGTGAGCCGAGATCGCACCATTGCACTCCAG
CCTGGGTGAAAACCGAAACTCCCTCTCAAAAATAAAATAAAATAAATACAGTAGTTTGTAAAATGATTCATCGGTAACATGGATGCAGCTATTTT
TAATCCTTATATGAAAATTGTATGCAGGGGAAAACATGTGAAGATAAAAGACATATACCTACTTAAAATTAGGTACTTATGTGAGGACAG
GGCCTAAGAAATAATAATATATATTAAAAAAGACTTGGATATTGGTGACTTTTTTTTCAACATTTTCTTGTTACATGAATTAGCCATTAAAAAAAG
AAAGATGGCTGCTCTACAATTTCTTTTCAGTGATCTGTGGTTCTTGTCCCTTGTGATGAGAGACCTGTAACTGTAAGTTTTATTCCTTTG
TTTGGCTAACTCATGTTTGACTTCCCTCTTC

IVS1                                                                              IVS2
---●                                                                              ●---
CTAGTGTGATTGGATCATGGCCATTTCTAAAGTCTTTGAACTGGGATTAGTTGCGGTGAGAGACCTTTGTTTCTTTTGATCACTCTCAATTTTA
 V  I  W  I  M  A  I  S  K  V  F  E  L  G  L  V  A
                      C

```
                                                                                                IVS4
                                                                                                ---●
TCAGAGGGGGCGGGGAGCCGTGGAGAGAGAAAGGGAAGTGGAAATTTCAGACCCAAGCTATCGCAGCTTACCTGTTCATTCTCAGAACTGT
                      E                                                                    N   C

GGGTCTGTGCCCCATGACACCTGGCTGCCCAAGAAGTGTTCCCTGTAAATGCTGGCACGGTCAGCTGCTTCCCTCAGGCATTTCTACCC
 G   S   V   P   H   D   T   W   L   P   K   K   C   S   L   C   K   C   W   H   G   Q   L   R   C   F   P   Q   A   F   L   P

IVS5
      ●---
GGCTGTGGTAAGGCGGAGGTTCTCCTCTTTGCCCTTTGAAGTTACGTAGTTGCCTTGGGGGTGCTTAGTTAGCAGGCTCTCCTTGTACC
 G   C

TCTTGTCTTGCTAGAGCCTGGCAGCCAAAGTTCTGCTTATAAAGCATCGCAGACTCCTGATGAGATAGTTGCCTCTCTTTGATATTTATTT
CCTCGGAACCTGGCTCTCTTGCTAGTCCTGCTGCCTTTCAGATAGATGTATTTCAAGTCTCTATTTGACATTTTATGTGTCTGAACTTCTATTGAGGAAATAA
ACAAGTCTCGGTCTCTTGTTAACCAAGAGATGTTCTCTGGTGTTCCTTTCCTTGGGTAGGGGGACCCAAACCAGGATGGGCAGCTCATTTAGA
GCCCACCCTGACGACAAATTCTATCAGAGGCTTGGCCCCCTTGCTAGTCCTTTAGAAACTTCCAGAGTCCTTTGAAAGTCCCTGGTAACCCCCTCCCCA
TACCTTACCACTGACTGGTCACAGAACCCTTACCATGACAGTCCTCTCCACCCTAGAACCCAGGAAGTAAATGAAAGCAAACATTTCACTGAGAACAGGAAGAATTCCCC
AGAAGGGCAGCACCTGAGAGGAAGATGTAGAACATTCAAGCCCCAGGAAGTAAATGAAAGCAAACATTTCACTGAGAACAGGAAGAATTCCCC
ATAGTTCTGGGCCTTGGAGAGATTGTGTCTTTGCCATTTGCATCCCGGGTGTCAGGCTCAGGATAGTGTTTGATAAGTGTGGGTGGGTGATTGGATGTGTAG
AATCCAGACAGGGATTGTGTCTTTGCCATTTGCATCCCGGGTGTCAGGCTCAGGATAGTGTTTGATAAGTGTGGGTGGGTGATTGGATGTGTAG
GGAACATTTGCTCTTCCTGGAACATGGGCCCAAGTCAGAATCTAACCCAGGTTGTGCTCATTCCTGCAAGTGAAGGCATCACCACTGGGCTAGGT
TCCAGGTGTGAGTGCCTGAGAAGAGCAGGTTCACAGTAGCGTATAGATATGCCACATTTGTGGGCAGCAGGATGAACTGCCAGAGAGGTTTGCTT
```

FIG. 2D.

```
                                IVS5
                                ---●
TAATGACCAAGCATCCCTACCTTCCAGATGGCCTTGTGATGGATGAGCACCTCGTGGCTTCCAGAACTCCAGGACTCCAGAACTACCACCGTCTGCACGTACTA
                                 D  G  L  V  M  D  E  H  L  V  A  S  R  T  P  E  L  P  P  S  A  R  T
                                                                                T
                  C                                           T
CCATTTTTATGCTAGTTGGCATCTGCCTTTCTATACAAGTACTATTAATCGACATTGACCTATTTCCAGAAATACAATTTTAGATATCATGCAA
 T  T  F  M  L  V  G  I  C  L  S  I  Q  S  Y  Y
          A
                                                            C
ATTTCATGACCAGTAAAGGCTGCTGCTACAATGTCCTAAACTGAAAGATGATCATTTGTAGTTGCCTTAAAATAATGAATACAATTTCAAAAATGGT

AACT               C
CTCCTAACATTCCCTACAGAACTACTTCTTCTTTTGCCCTCTCCCAAAAAACTACTTCTTTTTTCAAAAGAAAGTCAGCCATATCTCC
                                         △△△△△                                                               C
ATTGTGCCTAAGTCCAGTGTTCTTTTTTTTTTTTTTGAGACGGAGTCTCACTCTGTCACCAGGCTGGACTGCAATGACGGCGATCTTGGTTC
                                                                                    △  G
  C                                                                          C
ACTGCAACCTCCGATCCGGGTTCAAGCCATTCTCCTGCCTAAGCCTCCCAAGTAACTGGGATTACAGGCATGTGTCACCATGCCCAGCTAATTT
                                                                   C                       △       △    △       △
TTTGTATTTTTAGTAGAGATGGGGGTTTCACCATATTGGCCAGTCTCGGAACTCCTGACCTTGTGATCCACTCGCCTCAGCCTCTCGAAGT
                                                △
GCTGAGATTACACACGTGAGCAACTGTGCAAGGCCTGGTGTTTCTTGATACATGTAATTCTACCAAGTCTTCTTAATATGTTCTTTTAAATGATT
```

FIG. 2E.

```
                         G
CAC
GAATTATATGTTCAGATTATTGGAGACTAATTCTAATGTGGACCCTTAGAATACAGTTTGAGTAGAGTTGATCAAAATCAATTAAAATAGTCTCTT

TAAAAGGAAAAGAAACATCTTTAAGGGGAGGAACCAGAGTGCTGAAGGAATGGAAGTCCATCTGCGTGTGCAGGGAGACTGGGTAGGAAAGAGGA

AGCAAATAGAAGAGAGGTTGAAAAACAAATGGGTTACTTGATTAGGTGGTGGTGTAGAGAAGCAAGTAAAAGGCTAAATGGAAGGGC
                                                                                 T
            G               G
AAGTTTCCATCATCTATAGAAAGCTATATAAGACAAGAACTCCCCTTTTTTCCCAAAGCATTATAAAAGAATGAAGCCTCCTTAGAAAAAAA
                                                                                   G
ATTATACCTCAATGTCCCCAACAAGATTGCTTAATAAATTGTGTTCCTCCAAGCTATTCAATTCTTTTAACTGTTGTGTAGAGACAAAATGTTCAC

AGTAAAAATGGAAA
AATATATTTAGTTGTAAACCAAGTGATCAAACTACATATTGTAAAGCCCATTTTTAAAAATACATTGTATATATGTGTATGCAC

AAAAAAAAAGGAAAACCACCCCTTAGGCAGGCAGGACATGCTCTCTTCAGAACTCTGCTCTTCAGAGTTCCAAAGAAGGATAA
CTATATTGACCTAAATGTGAACTGGTTATTCTAGGTGGTGAGGTGCTTTATGGTGGGGTTTTGCTCTCTTGATGCCCCTTTTTGCATTTTCCAAA

AACATCTTTTAT - CR-3
GTACCATGGTGAGGATGTGTTATATCTTTTCCAGGTCCTAAAAGTCCCTGGCAACTCCCCCTACCATGACTGGTCACAGAACCCTTT
```

FIG. 2F.

CACCTTTATTGATTTGTACTGATTTCATATGGAATATGGCAACTACATCTGGCTCAAAACAAAGGAAACCAGAGAGAGCCAAGTCCCAGGTGAGTGCTC

AGTTCTGTTTCTAGCTTTGACGTGTGTGTCTTCTCTGTGAAGGACAAAATTTGCTTCTATTATTTAGTACCATAATTTGTGTTTTCCAAATTAATT

CCCTGCAG ⊢ · CR - 1

FIG. 2G.

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1:

AATTGTTAAA GCTATGGACT GCAGGAAGAT GGCCC 35

( 2 ) INFORMATION FOR SEQ ID NO:2:

( i ) SEQUENCE CHARACTERISTICS:
        ( A ) LENGTH: 5761 base pairs
        ( B ) TYPE: nucleic acid
        ( C ) STRANDEDNESS: double
        ( D ) TOPOLOGY: linear ( x i ) SEQUENCE DESCRIPTION: SEQ ID NO:2:

| | | | | | |
|---|---|---|---|---|---|
| GCCGGCACTC | CCACTGGAGA | GTCCCAGCTG | CCTCTGGCCG | CCCCTCCCCT | CTCCCGGGCA | 60 |
| CCTGGCGCCG | CTCCCGCGTC | CTTTCAGGAA | TTCACGTCCG | CCTGGAATTT | GCACTTCAAG | 120 |
| TCTGGAGCCC | CCAAGGAACC | CCTCCTGACC | CTGAACTTCT | ATCTCAGTTT | CAAGCTTCCT | 180 |
| AGTCTTCCCC | ACACACACAC | ACCTAGCTCC | TCAGGCGGAG | AGCACCCCTT | TCTTGGCCAC | 240 |
| CCGGGTATCC | CCCAGGGAGT | ACGGGGCTCA | AAACACCCTT | CTGGAAAAAA | CAAAGGTGGA | 300 |
| AGCAAATTTC | AGGAAGTAAA | ACTTCTGAAA | TAAATAAAA | TATCGAATGC | CTTGAGACCC | 360 |
| ATACATTTTC | AGGTTTTCCT | AATTAAAGCA | ATTACTTCC | ACCACCCTC | CAACCTGGAA | 420 |
| TCACCAACTT | GATTAGAGAA | ACTGATTTTT | CTTTTTTCTT | TTTTTTCCC | GAAAAGAGTA | 480 |
| CCTCTGATCA | TTTTAGCCTG | CAACTAATGA | TAGAGATATT | AGGGCTAGTT | AACCACAGTT | 540 |
| TTACAAGACT | CCTCTTCCCG | CGTGTGGGCC | ATTGTCATGC | TGTCGGTCCC | GCCCACCTGA | 600 |
| AAGGTCTCCC | CGCCCCGACT | GGGGTTTGTT | GTTGAAGAAG | GAGAATCCCC | GGAAAGGCTG | 660 |
| AGTCTCCAGC | TCAAGGTCAA | AACGTCCAAG | GCCGAAAGCC | CTCCAGTTTC | CCCTGGACGC | 720 |
| CTTGCTCCTG | CTTCTGCTAC | GACCTTCTGG | GGAAAACGAA | TTTCTCATTT | TCTTCTTAAA | 780 |
| TTGCCATTTT | CGCTTTAGGA | GATGAATGTT | TTCCTTTGGC | TGTTTGGCA | ATGACTCTGA | 840 |
| ATTAAAGCGA | TGCTAACGCC | TCTTTTCCCC | CTAATTGTTA | AAAGCTATGG | ACTGCAGGAA | 900 |
| GATGGCCCGC | TTCTCTTACA | GGTATGAGCT | AATCTTAGAA | TAGTGAACTT | TTTTTGATTG | 960 |
| CTAGAGATTG | CCAGCTTAGG | AAGTAATGTT | CTACACTGTC | ATTTGATTTT | TCTCCTTGCT | 1020 |
| CAAGCCTTAA | AAGAGCTGCC | AACCGACTGC | TGTTTTTCCT | GAAAGACCTG | GAATTTCACA | 1080 |
| TGGTTACTTC | TAACTTTGCC | ATTGGCTTTT | AACATTTCG | TGTTAATGTT | AATTTTCATT | 1140 |
| TTATGTTAAT | GACTCTGCCT | ATGAAATAGT | GTTTCTTTAC | TTCTTGTACA | AATAAAGGTC | 1200 |
| AGTACTACAA | CCAAATTTAA | ATCTTCCGAA | AAGATTAAAG | GTATAAGCAG | ATTCAATACT | 1260 |
| TGGCAAAACT | ATTAAGATAA | TAGCAAAAAA | AAAAAAAAA | CCCACATTTT | TTACCTAAAA | 1320 |
| ACCTTTTAAG | TGATTGGTTA | AAATAGTTTG | GCCGGGTGCG | GTGGCTCACG | CCTGTAATCC | 1380 |
| TAGCACTTTG | GGAGGCAGAG | GCGGGTGGAT | CACTGAGGTC | AGGAGACCAG | CCTGGCCAAC | 1440 |
| ATGGCAAAAC | CCCGTCTCTA | TTAAAAATAC | AAAAATTAGC | CAAGCATGGT | GGCGGGCACC | 1500 |
| TGTAATCCCA | GCTACTCTGG | AGGCTGAGGC | AGGAGAATTG | CTTGAACTGG | GGAGGGGAGG | 1560 |
| CAGTGAGCCG | AGATCGCACC | ATTGCACTCC | AGCCTGGGTG | AAAAACCGAA | ACTCCCTCTC | 1620 |
| AAAAATAAAT | AATAAATAC | AGTAGTTTGT | AAAATGATTC | ATCGGTAACA | TGGGATGCAG | 1680 |
| CTATTTTTTA | ATCCTTATAT | GAAAATTGTA | TGCAGGGGAA | AACATGTGAA | ATAGAAGATA | 1740 |
| AAAGACATAT | ACCTACTTAA | AATTAGGTAC | TTATGTGAGG | ACAGGGCCTA | AGAAATAATA | 1800 |
| ATATATATTA | AAAAGACTTG | GATATTGGTG | ACTTTTTTTC | AACATTTTTC | TTTGTTACAT | 1860 |
| GAATTAGCCA | TTAAAAAAAG | AAAGATGGTG | CTCTACAATT | TCTTTTCAGT | GATCTGTGGT | 1920 |
| CTTGTCCTTG | TGATGAGAGG | ACCTGGGTGT | TAACTTGTAA | GGTTTATTT | CCTTTGTTTG | 1980 |

-continued

```
GCTAACTCAT GTTTGACTTC CTCTTCCTAG TGTGATTTGG ATCATGGCCA TTTCTAAAGT  2040
CTTTGAACTG GGATTAGTTG CCGGTGAGAG ACCTTTTGTT TCTTTTGATC ACTCTCAATT  2100
TTATGTGGCC TAAAATACAG ACTCCATGAA TTGATTTGTC GTTAAGGGCT GGGCCATCAG  2160
GAATTTGCTC GTCCATCTCG GGGATACCTG GCCTTCAGAG ATGACAGCAT TTGGCCCCAG  2220
GAGGAGCCTG CAATTCGGCC TCGGTCTTCC CAGCGTGTGC CGCCCATGGG GATACAGCAC  2280
AGTAAGAACT GCCTGACTTC GATGCTTCTG CCCTGGCCCT TCATGTGTCT CCTGACTATC  2340
TTTCCAACAC TCTTTCACCT AAAAGGGCAC CTGGTTCTGG AACTGTGCAG GTGCTGGACT  2400
GCTTTGGTTT TGGAAGTGAG ACAAGGATTG TGTATTTTAC TTCCCTAGAG TGCAGTTTCC  2460
TCCCCTGAGT CCACTTCACA CTGGGAACCC AGAACCACCA CTGGCCTATG CATGAAAATG  2520
ACTTCTCTGC TCAAGGCAC AGAGTCTTAC TCTGATACAA CACATTGGTG TTGTATTAAC  2580
CTTCGCTTAC AGGAATTGCC CTTGCACTTT TCCATCCCTA CACCTCAGTC ATTCTGTTCT  2640
TACCTTTCAA GGTAAGGAGC TAAACAGAAC CTGCTGCCTG AATGGGGGAA CCTGCATGCT  2700
GGGGTCCTTT TGTGCCTGCC CTCCCTCCTT CTACGGACGG AACTGTGAGC ACGATGTGCG  2760
CAAAGAGTAA GCAATTCAGA GGGGCGGGGA GCCGTGGAGA GGAGAGAGAA AGGGAAGTGG  2820
AAATTTCAGA CCCAAGCTAT CGCAGCTTAC CTGTTCATTC TCAGGAACTG TGGGTCTGTG  2880
CCCCATGACA CCTGGCTGCC CAAGAAGTGT TCCCTGTGTA AATGCTGGCA CGGTCAGCTC  2940
CGCTGCTTTC CTCAGGCATT CTACCCGGC TGTGGTAAGC GGAGGTTCTC CTCTTTCTTT  3000
TGCCCTTTGA AGTTACGTAG TTGCCTTGGG GGTGCTTAG TTAGCAGGCT CTCCTTGTAC  3060
CTCTTGTCTT GCTAGAGCCT GGCAGCCAAA GTTCTGCTTA TAAAAGCATC GCAGACTCCT  3120
GATGAGATAG TTGCCTTGGC CTCTTTGATA TTTATTTCCT CGGGAACCTG GCTAGTCCTG  3180
CTGCCTTTCA GATAGAGATG TATTTCAAGT CTATTTGACA TTTTATGGTC TGAACTTCTA  3240
TTGAGGAAAA TAAACAAGTC TCGGTCTCTT GTTAAACCAA GAGATGTTCT CTGGTGTTCC  3300
TTTCCTTTGG GTAGGGGGA CCCAAACCAG GATGGGCAGC TCATTTAGAG CCCACCCTGA  3360
CGACAAATTC TATCAGAGGC TTGGCCCCTT GCTAGTCCTT TAGAAACTTC CAGAGTCCTA  3420
AAAGTCCCTG GTAACCCCCT CCCCATACCT TACCATGACT GGTCACAGAA CCCTTACCAT  3480
GACTGGTCAC AGAACCCTTT CACCTTCTTG ATTTTTACT GATTGAGGA ATACAATGAA  3540
AAGAAGGGCA GCACCTGGAG AGGAAAAGAG GCGACAGTCC TCTCTCCACC CTAGCCTGAG  3600
CCAGGTTTCT AGGGCCCCCC AAATTCAGAG ACCTATTATA GTTCTGGGCC TTGGAGATGT  3660
AGAAATGGAA AATATTCAAG CCCAGGAAGT AAATGAAAGC AAACATTTCA CTGAGAACAG  3720
GAAGGAATTC CCCAATCCAG ACAGGGATTG TGTCTTTGCC ATTTGCATCC TGGGTGTCAG  3780
GCTCAGGATA GGTGTTTGAT AAGTGTGGGT TGGGTGATTG GATGTGTAGG AACATTTGC  3840
TCTTCCTGGA ACATGGGGCC CAAGTCAGAA TCTAACCCAG GTTGTGCTCA TTCCTGCAAG  3900
TGAAGGCATC ACCACTGGGC TAGGTTCCAG GTGTGAGTGT CCTGAGAAGA GCAGGTTCAC  3960
AGTAGCGTAT AGATATGCCA CATTTGTGGG CAGCAGGATG AACTGCCAGA GAGGTTTGCT  4020
TTAATGACCA AGCATCCCTA CCTTCCAGAT GGCCTTGTGA TGGATGAGCA CCTCGTGGCT  4080
TCCAGGACTC CAGAACTACC ACCGTCTGCA CGTACTACCA CTTTATGCT AGTTGGCATC  4140
TGCCTTTCTA TACAAAGCTA CTATTAATCG ACATTGACCT ATTTCCAGAA ATACAATTTT  4200
AGATATCATG CAAATTTCAT GACCAGTAAA GGCTGCTGCT ACAATGTCCT AACTGAAAGA  4260
TGATCATTTG TAGTTGCCTT AAAATAATGA ATACAATTTC CAAAATGGTC TCTAACATTT  4320
CCTTACAGAA CTACTTCTTA CTTCTTTGCC CTGCCCTCTC CCAAAAAACT ACTTCTTTTT  4380
```

-continued

```
TCAAAAGAAA GTCAGCCATA TCTCCATTGT GCCTAAGTCC AGTGTTTCTT TTTTTTTTT      4440
TTTTTGAGAC GGACTCTCAC TCTGTCACCC AGGCTGGACT GCAATGACGC GATCTTGGTT      4500
CACTGCAACC TCCGCATCCG GGGTTCAAGC CATTCTCCTG CCTAAGCCTC CCAAGTAACT      4560
GGGATTACAG GCATGTGTCA CCATGCCCAG CTAATTTTTT TGTATTTTTA GTAGAGATGG      4620
GGGTTTCACC ATATTGGCCA GTCTGGTCTC GAACTCCTGA CCTTGTGATC CACTCGCCTC      4680
AGCCTCTCGA AGTGCTGAGA TTACACACGT GAGCAACTGT GCAAGGCCTG GTGTTTCTTG      4740
ATACATGTAA TTCTACCAAG GTCTTCTTAA TATGTTCTTT TAAATGATTG AATTATATGT      4800
TCAGATTATT GGAGACTAAT TCTAATGTGG ACCTTAGAAT ACAGTTTTGA GTAGAGTTGA      4860
TCAAAATCAA TTAAATAGT CTCTTTAAAA GGAAAGAAAA CATCTTTAAG GGGAGGAACC       4920
AGAGTGCTGA AGGAATGGAA CTCCATCTCC GTGTGTGCAG GGAGACTGGG TAGGAAAGAG      4980
GAAGCAAATA GAAGAGAGAG GTTGAAAAAC AAAATGGGTT ACTTGATTGG TGATTAGGTG      5040
GTGGTAGAGA AGCAAGTAAA AAGGCTAAAT GGAAGGGCAA GTTCCATCA TCTATAGAAA       5100
GCTATATAAG ACAAGAACTC CCCTTTTTTT CCCAAAGGCA TTATAAAAG AATGAAGCCT       5160
CCTTAGAAAA AAAATTATAC CTCAATGTCC CCAACAAGAT TGCTTAATAA ATTGTGTTTC      5220
CTCCAAGCTA TTCAATTCTT TTAACTGTTG TAGAAGACAA AATGTTCACA ATATATTTAG      5280
TTGTAAACCA AGTGATCAAA CTACATATTG TAAAGCCCAT TTTTAAAATA CATTGTATAT      5340
ATGTGTATGC ACAGTAAAAA TGGAAACTAT ATTGACCTAA ATGTGAACTG GTTATTTCTA      5400
GGTGGTGAGG TGCTTTATGG TGGTGGGTTT TGCTCTTGA TGCCCTTTTT GCATTTTCCA       5460
AAGTACCATG GTGAGGATGT GTTATATCTT TTCCAGGGTC CTAAAAGTCC CTGGCAACTC      5520
CCTCCCCATA CCCTACCATG ACTGGTCACA GAACCCTTTC ACCTTATTGA TTTGTACTGA      5580
TTTCATATGG AATATGGCAA CTACATCTGG CTCAAAACAA AGGAAACCAG AAGAGCCAAG      5640
TCCCAGGTGA GTGCTCAGTT CTGTTTCTAG CTTTGACGTG TGTGTTCTTC TGTGAAGGAC      5700
AAAATTTGCT TCTATTATTT AGGTACCATA ATTTGTGTTT TTCCAAATTA ATTCCCTGCA      5760
G                                                                     5761
```

( 2 ) INFORMATION FOR SEQ ID NO:3:

( i ) SEQUENCE CHARACTERISTICS:
        ( A ) LENGTH: 188 amino acids
        ( B ) TYPE: amino acid
        ( D ) TOPOLOGY: linear ( i i ) MOLECULE TYPE: protein ( x i ) SEQUENCE DESCRIPTION: SEQ ID NO:3:

```
Met Asp Cys Arg Lys Met Ala Arg Phe Ser Tyr Ser Val Ile Trp Ile
 1               5                  10                   15

Met Ala Ile Ser Lys Val Phe Glu Leu Gly Leu Val Ala Gly Leu Gly
                20                  25                  30

His Gln Glu Phe Ala Arg Pro Ser Arg Gly Tyr Leu Ala Phe Arg Asp
            35                  40                  45

Asp Ser Ile Trp Pro Gln Glu Pro Ala Ile Arg Pro Arg Ser Ser
        50                  55                  60

Gln Arg Val Pro Pro Met Gly Ile Gln His Ser Lys Glu Leu Asn Arg
 65                  70                  75                  80

Thr Cys Cys Leu Asn Gly Gly Thr Cys Met Leu Gly Ser Phe Cys Ala
                85                  90                  95

Cys Pro Pro Ser Phe Tyr Gly Arg Asn Cys Glu His Asp Val Arg Lys
               100                 105                 110
```

```
Glu Asn Cys Gly Ser Val Pro His Asp Thr Trp Leu Pro Lys Lys Cys
        115                 120                 125

Ser Leu Cys Lys Cys Trp His Gly Gln Leu Arg Cys Phe Pro Gln Ala
        130                 135                 140

Phe Leu Pro Gly Cys Asp Gly Leu Val Met Asp Glu His Leu Val Ala
145                 150                 155                 160

Ser Arg Thr Pro Glu Leu Pro Pro Ser Ala Arg Thr Thr Thr Phe Met
                165                 170                 175

Leu Val Gly Ile Cys Leu Ser Ile Gln Ser Tyr Tyr
                180                 185
```

( 2 ) INFORMATION FOR SEQ ID NO:4:

( i ) SEQUENCE CHARACTERISTICS:
        ( A ) LENGTH: 2675 base pairs
        ( B ) TYPE: nucleic acid
        ( C ) STRANDEDNESS: double
        ( D ) TOPOLOGY: linear ( i x ) FEATURE:
        ( A ) NAME/KEY: CDS
        ( B ) LOCATION: 809..1372

( x i ) SEQUENCE DESCRIPTION: SEQ ID NO:4:

```
AAGCTTGCGC GCCATGTAAG GTAAAGTGAC TGATTCTATA GCAATCCAAT TGTTCCTTTG      60

TCTGCCCGTT TACATATAAC AATGTTGTCA ATGTTTGATT GAAAATACCT AGCAGGTGAC     120

ACACACACAC CTAGCTCCTC AGGCGGAGAG CACCCCTTTC TTGGCCACCC GGGTATCCCC     180

CAGGGAGTAC GGGGCTCAAA ACACCCTTTT GGAGAACAAG GTGGAAGCAA ATTTCAGGAA     240

GTAAAACTTC CGAAATAAAA TAAAATATCG AATGCCTTGA GACCCATACA TTTTCAGGTT     300

TTCCTAATTA AAGCAATTAC TTTCCACCAC CCCTCCAACC TGGAATCACC AACTTGGTTA     360

GAGAAACTGA TTTTTCTTTT TTCTTTTTTT TTCCCAAAAG AGTACATCTG ATCATTTTAG     420

CCTGCAACTA ATGATAGAGA TATTAGGGCT AGTTAACCAC AGTTTTACAA GACTCCTCTC     480

CCGCGTGTGG GCCATTGTCA TGCTGTCGGT CCCGCCCACC TGAAAGGTCT CCCCGCCCCG     540

ACTGGGGTTT GTTGTTGAAG AAGGAGAATC CCCGGAAAGG CTGAGTCTCC AGCTCAAGGT     600

CAAAACGTCC AAGGCCGAAA GCCCTCCAGT TTCCCCTGGA CACCTTGCTC CTGCTTCTGC     660

TACGACCTTC TGGGAACGCG AATTTCTCAT TTTCTTCTTA AATTGCCATT TTCGCTTTAG     720

GAGATGAATG TTTTCCTTTG GCTGTTTTGG CAATGACTCT GAATTAAAGC GATGCTAACG     780

CCTCTTTTCC CCCTAATTGT AAAAGCT ATG GAC TGC AGG AAG ATG GTC CGC        832
                                Met Asp Cys Arg Lys Met Val Arg
                                 1               5

TTC TCT TAC AGT GTG ATT TGG ATC ATG GCC ATT TCT AAA GCC TTT GAA      880
Phe Ser Tyr Ser Val Ile Trp Ile Met Ala Ile Ser Lys Ala Phe Glu
        10                  15                  20

CTG GGA TTA GTT GCC GGG CTG GGC CAT CAA GAA TTT GCT CGT CCA TCT      928
Leu Gly Leu Val Ala Gly Leu Gly His Gln Glu Phe Ala Arg Pro Ser
25                  30                  35                  40

CGG GGA GAC CTG GCC TTC AGA GAT GAC AGC ATT TGG CCC CAG GAG GAG      976
Arg Gly Asp Leu Ala Phe Arg Asp Asp Ser Ile Trp Pro Gln Glu Glu
                45                  50                  55

CCT GCA ATT CGG CCT CGG TCT TCC CAG CGT GTG CTG CCC ATG GGA ATA     1024
Pro Ala Ile Arg Pro Arg Ser Ser Gln Arg Val Leu Pro Met Gly Ile
                60                  65                  70

CAG CAC AGT AAG GAG CTA AAC AGA ACC TGC TGC CTG AAT GAG GGA ACC     1072
Gln His Ser Lys Glu Leu Asn Arg Thr Cys Cys Leu Asn Glu Gly Thr
```

-continued

|  |  | 75 |  |  |  |  | 80 |  |  |  |  | 85 |  |  |  |
|---|---|---|---|---|---|---|---|---|---|---|---|---|---|---|---|
| TGC | ATG | CTG | GGG | TCC | TTT | TGT | GCC | TGC | CCT | CCC | TCC | TTC | TAC | GGA | CGG | 1120 |
| Cys | Met | Leu | Gly | Ser | Phe | Cys | Ala | Cys | Pro | Pro | Ser | Phe | Tyr | Gly | Arg |
|  | 90 |  |  |  |  | 95 |  |  |  |  | 100 |  |  |  |  |
| AAC | TGT | GAG | CAC | GAT | GTG | CGC | AAA | GAG | AAC | TGT | GGG | TCT | GTG | CCC | CAT | 1168 |
| Asn | Cys | Glu | His | Asp | Val | Arg | Lys | Glu | Asn | Cys | Gly | Ser | Val | Pro | His |
| 105 |  |  |  | 110 |  |  |  |  | 115 |  |  |  |  | 120 |  |
| GAC | ACC | TGG | CTG | CCC | AAG | AAG | TGT | TCC | CTG | TGT | AAA | TGC | TGG | CAC | GGT | 1216 |
| Asp | Thr | Trp | Leu | Pro | Lys | Lys | Cys | Ser | Leu | Cys | Lys | Cys | Trp | His | Gly |
|  |  |  |  | 125 |  |  |  |  | 130 |  |  |  |  | 135 |  |
| CAG | CTC | CGC | TGC | TTT | CCT | CAG | GCA | TTT | CTA | CCC | GGC | TGT | GAT | GGC | CTT | 1264 |
| Gln | Leu | Arg | Cys | Phe | Pro | Gln | Ala | Phe | Leu | Pro | Gly | Cys | Asp | Gly | Leu |
|  |  | 140 |  |  |  |  | 145 |  |  |  |  | 150 |  |  |  |
| GTG | ATG | GAT | GAG | CAC | CTC | GTG | GCT | TCC | AGG | ACT | CCA | GAA | CTA | CCA | CCG | 1312 |
| Val | Met | Asp | Glu | His | Leu | Val | Ala | Ser | Arg | Thr | Pro | Glu | Leu | Pro | Pro |
|  |  | 155 |  |  |  |  | 160 |  |  |  |  | 165 |  |  |  |
| TCT | GCA | CGT | ACT | ACC | ACT | TTT | ATG | CTA | GCT | GGC | ATC | TGC | CTT | TCT | ATA | 1360 |
| Ser | Ala | Arg | Thr | Thr | Thr | Phe | Met | Leu | Ala | Gly | Ile | Cys | Leu | Ser | Ile |
|  |  | 170 |  |  |  |  | 175 |  |  |  |  | 180 |  |  |  |
| CAA | AGC | TAC | TAT | TAATCGACAT | TGACCTATTT | CCAGAAATAC | AATTTAGAT |  |  |  |  |  |  |  |  | 1412 |
| Gln | Ser | Tyr | Tyr |
| 185 |

| ATTATGCAAA | TTTCATGACC | CGTAAAGGCT | GCTGCTACAA | TGTCCTAACT | GAAAGATGAT | 1472 |
| CATTTGTAGT | TGCCTTAAAA | TAATGAATAC | AATTTCCAAA | ACGGTCTCTA | ACATTTCCTT | 1532 |
| ACAGAACTAA | CTACTTCTTA | CCTCTTTGCC | CTGCCCTCTC | CCAAAAAACT | ACTTCTTTTT | 1592 |
| TCAAAGAAA | GTCAGCCATA | TCTCCATTGT | GCCCAAGTCC | AGTGTTTCTT | TTTTTTTTT | 1652 |
| GAGACGGACT | CTCACTCTGT | CACCCAGGCT | GGACTGCAAT | GACGCGATCT | TGGTTCACCG | 1712 |
| CAACCTCCGC | ATCCGGGGTT | CAAGCCATTC | TCCTGCCTCA | GCCTCCAAG | TAGCTGGGAT | 1772 |
| TACAGGCATG | TGTCACCATG | CCGGCTAATT | TTTTGTATT | TTAGTAGAG | ACGGGGTTT | 1832 |
| CACCATATTG | GCCAGTCTGG | TCTCGAACTC | TGACCTTGTG | ATCCATCGCT | CGCCTCTCAA | 1892 |
| GTGCTGAGAT | TACACACGTG | AGCAACTGTG | CAAGGCCTGG | TGTTTCTTGA | TACATGTAAT | 1952 |
| TCTACCAAGG | TCTTCTTAAT | ATGTTCTTTT | AAATGATTGA | ATTATACACT | CAGATTATTG | 2012 |
| GAGACTAAGT | CTAATGTGGA | CCTTAGAATA | CAGTTTTGAG | TAGAGTTGAT | CAAAATCAAT | 2072 |
| TAAAATAGTC | TCTTTAAAAG | GAAAGAAAAC | ATCTTTAAGG | GGAGGAACCA | GAGTGCTGAA | 2132 |
| GGAATGGAAC | TCCATCTCCG | TGTGTGCAGG | GAGACTGGGT | AGGAAAGAGG | AAGCAAATAG | 2192 |
| AAGAGAGAGG | TTGAAAAACA | AAATGGGTTA | CTTGATTGGT | GATTAGGTGG | TGGTAGAGAA | 2252 |
| GCAAGTAAAA | AGGCTAAATG | GAAGGGCAAG | TTTCCATCAT | CTATAGAAAG | CTATGTAAGA | 2312 |
| CAAGGACTCC | CCTTTTTTC | CCAAAGGCAT | TGTAAAAAGA | ATGAAGTCTC | CTTAGAAAAA | 2372 |
| AAATTATACC | TCAATGTCCC | CAACAAGATT | GCTTAATAAA | TTGTGTTTCC | TCCAAGCTAT | 2432 |
| TCAATTCTTT | TAACTGTTGT | AGAAGAGAAA | ATGTTCACAA | TATATTTAGT | TGTAAACCAA | 2492 |
| GTGATCAAAC | TACATATTGT | AAAGCCCATT | TTTAAAATAC | ATTGTATATA | TGTGTATGCA | 2552 |
| CAGTAAAAAT | GGAAACTATA | TTGACCTAAA | AAAAAAAAA | GGAAACCACC | TTAGGCAGG | 2612 |
| CAGGACATGC | TCTTCAGAAC | TCTGCTCTTC | AGAGTTCCAA | AGAAGGGATA | AAACATCTTT | 2672 |
| TAT |  |  |  |  |  | 2675 |

( 2 ) INFORMATION FOR SEQ ID NO:5:

( i ) SEQUENCE CHARACTERISTICS:
        ( A ) LENGTH: 188 amino acids
        ( B ) TYPE: amino acid (D) TOPOLOGY: linear (ii) MOLECULE TYPE: protein (xi) SEQUENCE DESCRIPTION: SEQ ID NO:5:

```
Met Asp Cys Arg Lys Met Val Arg Phe Ser Tyr Ser Val Ile Trp Ile
 1               5                  10                 15
Met Ala Ile Ser Lys Ala Phe Glu Leu Gly Leu Val Ala Gly Leu Gly
            20                  25                 30
His Gln Glu Phe Ala Arg Pro Ser Arg Gly Asp Leu Ala Phe Arg Asp
         35                  40                 45
Asp Ser Ile Trp Pro Gln Glu Glu Pro Ala Ile Arg Pro Arg Ser Ser
        50                  55                 60
Gln Arg Val Leu Pro Met Gly Ile Gln His Ser Lys Glu Leu Asn Arg
 65                 70                  75                 80
Thr Cys Cys Leu Asn Glu Gly Thr Cys Met Leu Gly Ser Phe Cys Ala
                85                  90                 95
Cys Pro Pro Ser Phe Tyr Gly Arg Asn Cys Glu His Asp Val Arg Lys
            100                 105                110
Glu Asn Cys Gly Ser Val Pro His Asp Thr Trp Leu Pro Lys Lys Cys
        115                 120                 125
Ser Leu Cys Lys Cys Trp His Gly Gln Leu Arg Cys Phe Pro Gln Ala
    130                 135                 140
Phe Leu Pro Gly Cys Asp Gly Leu Val Met Asp Glu His Leu Val Ala
145                 150                 155                160
Ser Arg Thr Pro Glu Leu Pro Pro Ser Ala Arg Thr Thr Thr Phe Met
            165                 170                 175
Leu Ala Gly Ile Cys Leu Ser Ile Gln Ser Tyr Tyr
            180                 185
```

HUMAN CRIPTO-RELATED GENE AND METHOD OF MEASURING CR-3

This application is a division of application Ser. No. 98/154,198, filed Nov. 17, 1993, which is a division of application Ser. No. 07/749,001, filed Aug. 23, 1991, now U.S. Pat. No. 5,264,557, all of which are hereby incorporated in their entirety by reference.

BACKGROUND OF THE INVENTION

1. Field of the Invention

The present invention relates, in general, to a human CRIPTO-related gene. In particular, the present invention relates to a DNA segment encoding a human CRIPTO-related gene; polypeptides encoded by the DNA segment; recombinant DNA molecules containing the DNA segment; cells containing the recombinant DNA molecule; a method of producing a human CRIPTO-related polypeptide; a DNA segment encoding a genomic clone of the human CRIPTO gene (CR-1); antibodies specific to CR-3; and a method of measuring the amount of CR-3 in a sample.

2. Background Information

Polypeptide growth factors play a role in stimulating cell proliferation. Their genes are expressed in the developing embryo, in normal adult tissues and in tumor cells (for review see Devel, T. F., *Ann. Rev. Cell Biol.* (1987) 3:443–492; Sporn, M. B. et al., *Nature* (1987) 332:217–219; Whitman, M. et al., *Ann. Rev. Biol.* (1989) 5:93–117). Characterization of these factors and sequencing of their genes have permitted their grouping into a relatively small number of families on the basis of sequence similarities (Mercola, M. et al., *Development* (1988) 108:451–460). One of these is the epidermal growth factor (EGF) family. EGF (Savage, C. R. et al., *J. Biol. Chem.* (1972) 247:7612–7621), transforming growth factor α (TGFα) (Derynck, R. et al., *Cell* (1984) 38:287–297) and amphiregulin (AR) (Plowman, G. D. et al., *Mol. Cell Biol.*, (1990) 10:1969–1981) share structural similarities including the conservation of six cystsines of the "EGF motif", which in EGF are involved in three disulfide bonds defining the tertiary structure. The presence of "EGF motif" also in developmental genes, such as Notch in Drosophila (Kidd, S. et al., *Mol. Cell. Biol.* (1986) 6:3094–3108) and lin-12 in *C. elegans* (Greenwald, L. *Cell* (1985) 43:583–590), may imply a novel role for the growth factors of the "EGF family." It has been suggested that they may exert their action on the cell surface during development to mediate cell-cell interactions by recognizing a complementary receptor on another cell.

Previously, the isolation of a human cDNA, referred to as CRIPTO (CR-1)(Ciccodicola, A. et al., *EMBO J.* (1989) 8:1987–1991), encoding a protein of 188 amino acids was described. The central portion of this protein shares structural similarities with the human TGFα (Derynck, R. et al., *Cell* (1984) 38:287–297), human AR (Plowman, G. D. et al., *Mol. Cell Biol.*, (1990) 10:1969–1981) and human EGF (Savage, C. R. et al., *J. Biol. Chem.* (1972) 247:7612–7621). Northern blot analysis of a wide variety of tumor and normal cell lines and tissues (e.g., choriocarcinoma, fibroblast, neuroblastoma, HeLa, placenta and testis) has shown that CRIPTO transcripts are detected only in undifferentiated human NTERA-2 clone D1 (NT2/D1) and mouse (F9) teratocarcinoma cells and these disappear after inducing the cells to differentiate with retinoic acid treatment (Ciccodicola, A. et al., *EMBO J.* (1989) 8:1987–1991).

SUMMARY OF THE INVENTION

It is a general object of this invention to provide a human CRIPTO-related gene (CR-3).

It is a specific object of this invention to provide a DNA segment which encodes a human CRIPTO-related gene (CR-3).

It is a further object of the invention to provide a polypeptide corresponding to a human CRIPTO-related gene (CR-3).

It is another object of the invention to provide a recombinant DNA molecule comprising a vector and a DNA segment encoding a human CRIPTO-related gene (CR-3).

It is a further object of the invention to provide a cell that contains the above-described recombinant molecule.

It is another object of the invention to provide a method of producing a polypeptide encoding a human CRIPTO-related gene (CR-3).

It is a further object of the invention to provide a genomic DNA segment coding for a polypeptide comprising an amino acid sequence corresponding to a human CRIPTO gene (CR-1).

It is a further object of the invention to provide antibodies having binding affinity to a human CRIPTO-related gene (CR-3), or a unique portion thereof and not to CR-1, or a unique portion thereof.

It is a further object of the invention to provide a method of measuring the amount of CR-3 in a sample.

Further objects and advantages of the present invention will be clear from the description that follows.

In one embodiment, the present invention relates to a DNA segment coding for a polypeptide comprising an amino acid sequence corresponding to a human CRIPTO-related gene CR-3.

In another embodiment, the present invention relates to a polypeptide free of proteins with which it is naturally associated and comprising an amino acid sequence corresponding to a human CRIPTO-related gene (CR-3).

In a further embodiment, the present invention relates to a recombinant DNA molecule comprising a vector and a DNA segment that codes for a polypeptide comprising an amino acid sequence corresponding to a human CRIPTO-related gene (CR-3).

In yet another embodiment, the present invention relates to a cell that contains the above-described recombinant DNA molecule.

In a further embodiment, the present invention relates to a method of producing a polypeptide comprising an amino acid sequence corresponding to a human CRIPTO-related gene (CR-3).

In another embodiment, the present invention relates to a genomic DNA segment coding for a polypeptide comprising an amino acid sequence corresponding to a human CRIPTO gene (CR-1).

In yet another embodiment, the present invention relates to an antibody having binding affinity to a human CRIPTO-related gene (CR-3), or a unique portion thereof and not to CR-1, or a unique portion thereof.

In a further embodiment, the present invention relates to a method of measuring the amount of CR-3 in a sample, comprising contacting the sample with the above-described antibodies and measuring the amount of immunocomplexes formed between the antibodies and any CR-3 in the sample.

BRIEF DESCRIPTION OF THE DRAWINGS

FIG. 1. CRIPTO-related sequences in human and mouse DNA. In FIG. 1A, 10 µg of genomic DNA was digested with EcoRI (E), PstI (P) and EcoRI+PstI (E/P), and sizefractionated by agarose gel electrophoresis. Hybridization probes are $^{32}$P-nick-translated 2B3 and G2 segments. The molecular weight markers included are HindIII/EcoRI-digested Lambda DNA. In FIG. 1B, 10 μg of mouse (first three lanes from left) and chicken DNA (fourth and fifth lanes) was digested with PstI (P), BamHI (B) and EcoRI (E). Hybridization probe is $^{32}$P-nick-translated 2B3 segment. Electrophoresis, transfer and hybridization were as described below except for washing conditions (2× SSC at 60° C.).

Figure 2C:
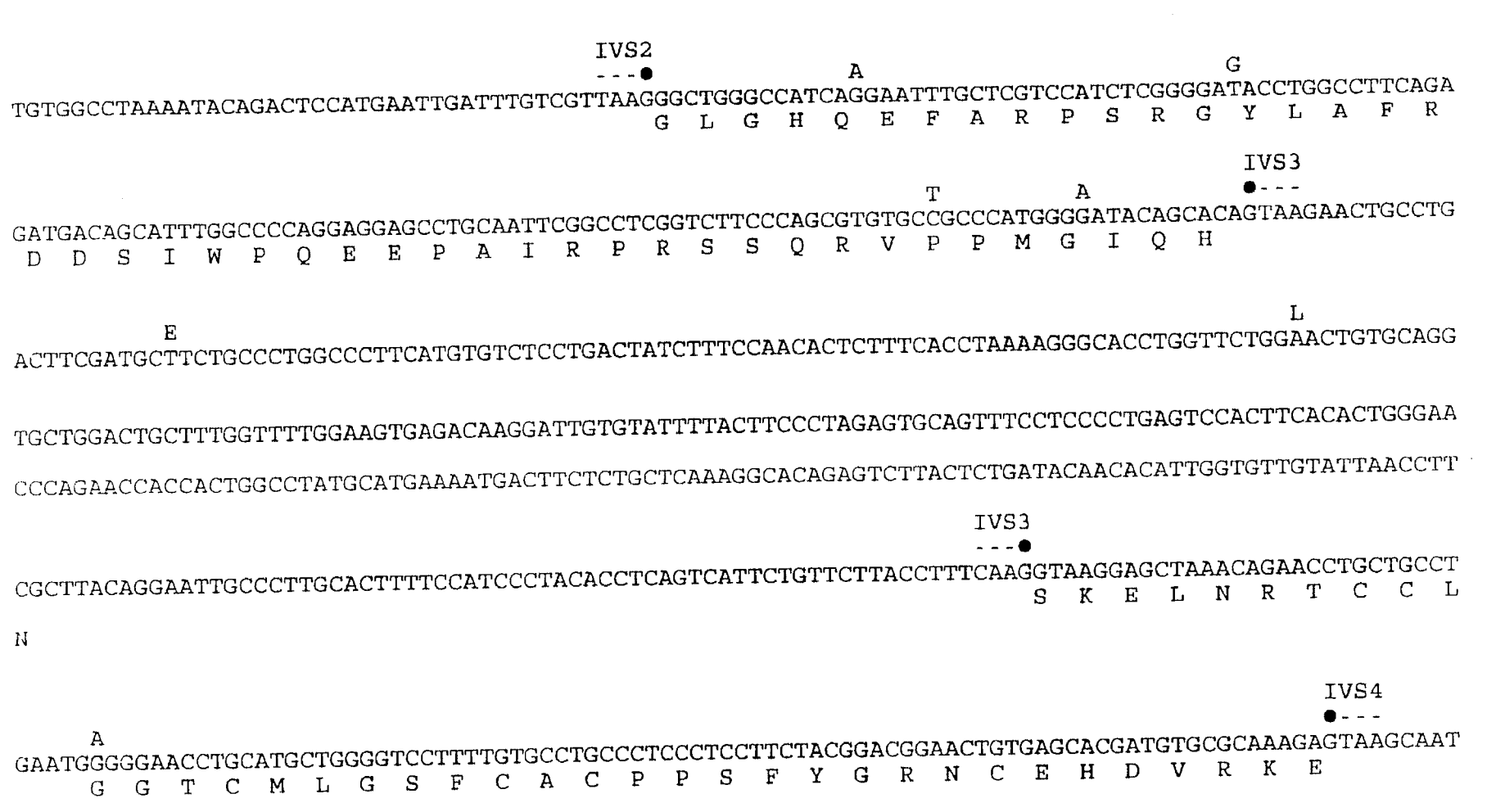

FIGS. 2A–2G. Nucleotide sequence of CR-1 and CR-3 genomic DNAe. The sequence of 5763 nucleotides of the CR-1 gene is shown. The nucleotides are numbered from the start codon and the amino acids for CR-1 are shown below. The nucleotide sequence of CR-3 is shown on top of CR-1. Nucleotide changes and deletions (Δ) in the CR-3 sequence are indicated above the CR-1 sequence. The six amino acid changes are indicated below the CR-1 protein sequence. It is to be noted that all the introns of CR-1 are absent in the CR-3 sequence. The boxed motifs are Sp1 binding, sites (solid-line boxes), pyrimidine stretches (thin-line boxes) and poly-adenylation signals (broken-line box). The vertical arrows indicate the multiple transcription starts. The Alu sequence present in the mRNA is underlined.

DETAILED DESCRIPTION OF THE INVENTION

Figure 1C:
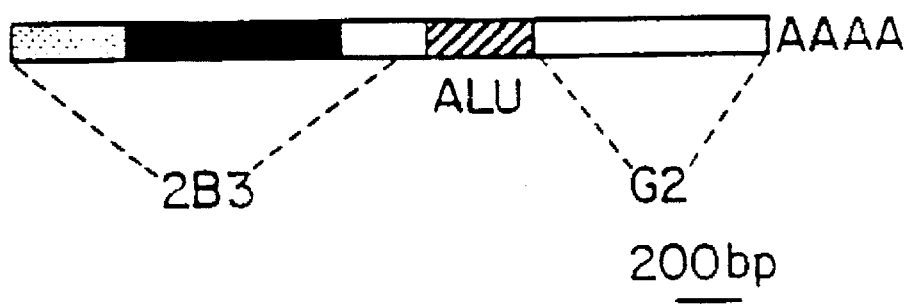
FIG. 1C shows schematic representation of human CRIPTO cDNA. The coding region is indicated by a solid box; AAAA indicates the poly(A) tail. cDNA regions corresponding to 2B3 and G2 probes are indicated.

The present invention relates to a human CRITPO-related gene. This novel human gene (designated CR-3) has been isolated and cloned from a human genomic library using a human CRIPTO cDNA fragment. The CR-3 gene sequence is identical to the human CRIPTO gene sequence with the exception of eight base pair substitutions that give rise to six amino acid changes in the sequence of the protein. The CR-3 human cDNA has been expressed in mammalian COS cells and the recombinantly produced protein can be used to study its biological properties and as an immunogen to generate monospecific antibodies.

CR-3 exhibits partial amino acid sequence homology and a tertiary structure within a 38 amino acid region similar to the EGF supergens family that includes EGF, TGFα, and amphiregulin. Since those peptides are potent mitogens that are involved in regulating the proliferation, differentiation, and transformation of various mesenchymal and epithelfal cells, CR-3 like CRIPTO can be expected to be a regulatory molecule that is involved in each of these processes. In addition, expression of CR-3 may serve as a tumor specific marker that may have applicability in the diagnosis, prognosis, and possible treatment of specific types of cancer. In this respect, CR-3 mRNA is expressed in several human colon cancer cell lines and possibly in human colorectal tumors.

In one embodiment, the present invention relates to DNA segment coding for a polypeptide comprising an amino acid sequence corresponding to a human CRIPTO-related gene (CR-3) and allelic and species variation thereof. In a preferred embodiment the DNA segment comprises the sequence shown in SEQ ID NO:4. In another preferred embodiment, the DNA segment encodes the amino acid sequence set forth in SEQ ID NO:5.

In another embodiment, the present invention relates to a polypeptide free of proteins with which it is naturally associated (or bound to a solid support) and comprising an amino acid sequence corresponding to a human CRIPTO-related gene (CR-3) and allelic and species variation thereof. In a preferred embodiment, the polypeptide comprises the amino acid sequence set forth in SEQ ID NO:5.

In another embodiment, the present invention relates to a recombinant DNA molecule comprising a vector (for example plasmid or vital vector) and a DNA segment coding for a polypeptide corresponding to CR-3, as described above. In a preferred embodiment, the encoding segment is present in the vector operably linked to a promoter.

In a further embodiment, the present invention relates to a cell containing the above described recombinant DNA molecule. Suitable host cells include procaryotes (such as bacteria, including E. coli) and both lower eucaryotes (for example yeast) and higher eucaryotes (for example, mammalian cells). Introduction of the recombinant molecule into the cell can be effected using methods known in the art.

In another embodiment, the present invention relates to a method of producing a polypeptide having an amino acid sequence corresponding to CR-3 comprising culturing the above-described cell under conditions such that the DNA segment is expressed and the polypeptide thereby produced and isolating the polypeptide.

In a further embodiment, the present invention relates to a DNA segment coding for a polypeptide comprising an amino acid sequence corresponding to a human CRIPTO gene (CR-1) wherein said DNA segment comprises the sequence shown in SEQ ID NO:2. The CR-1 genomic clone can be used in transgenic animals to examine the effects of overexpression of this gene on development and tumorigenicity and to study the regulation of this gene via sequences in the 5-flanking region that are upstream from the ATG translation initiation codon.

In yet another embodiment, the present invention relates to an antibody having binding affinity to a human CRIPTO-related gene (CR-3), or a unique portion thereof and not to CR-1, or a unique portion thereof. In one preferred embodiment, CR-3 has the amino acid sequence set forth in SEQ ID NO:5, or allelic or species variation thereof.

Antibodies can be raised to CR-3, or unique portions thereof, in its naturally occuring form and in its recombinant form. Additionally, antibodies can be raised to CR-3 in both its active form and inactive form, the difference being that antibodies to the active CR-3 are more likely to recognize epitopes which are only present in the active CR-3.

CR-3 may be joined to other materials, particularly polypeptides, as fused or covalently joined polypeptides to be used as immunogens. CR-3 or its fragments may be fused or covalently linked to a variety of immunogens, such as keyhole limpet hemocyanin, bovine serum albumin, tetanus toxoid, etc. See for example, Microbiology, Hoeber Medical Division (Harper and Row, 1969), Landsteiner, Specificity of Serological Reactions (Dover Publications, New York, 1962) and Williams et al., Methods in Immunology and Immunochemistry, Vol. 1 (Academic Press, New York, 1967), for descriptions of methods of preparing polyclonal antisera. A typical method involves hyperimmunization of an animal with an antigen. The blood of the animal is then collected shortly after the repeated immunizations and the gamma globulin is isolated.

In some instances, it is desirable to prepare monoclonal antibodies from various mammalian hosts. Description of techniques for preparing such monoclonal antibodies may be found in Stites et al., editors, Basic and Clinical Immunology, (Lange Medical Publications, Los Altos, Calif., Fourth edition) and references cited therein, and in particular in Kohler and Milstein in Nature 256:495–497 (1975), which discusses one method of generating monoclonal antibodies.

Antibodies having binding affinity to a human CRIPTO-related gene (CR-3), or a unique portion thereof and not to CR-1, or a unique portion thereof can be isolated using screening methods (for example, ELISA assays). Antibodies having binding affinity for CR-3 (with or without binding affinity for CR-1) can be used in immunoassays to detect CR-3.

In a further embodiment, the present invention relates to a method of measuring the amount of CR-3 in a sample, comprising contacting the sample with the above-described antibodies and measuring the amount of immunocomplexes formed between the antibodies and any CR-3 in the sample. Measuring the amount of immunoclomexes formed can be any of those well known in the art, such as RIA, ELISA, and direct and indirect immunoassays.

EXAMPLES

The following protocols and experimental details are referenced in the Examples that follow:

Southern blot analysis and chromosomal mapping panels.

All the hybrid cell lines were hamster x human obtained following a published protocol (Davidson, R. D., *Somatic Cell Gen.* (1976) 2:165–176). The hybrid clones were characterized for their human chromosome content (Rocchi, M. et al., *Hum. Gen*, (1986) 74:30–33).

DNA preparation from human peripheral blood lymphocytes and cell lines, restriction enzyme digestion, electrophoresis and Southern blotting were performed using standard techniques (Maniatis, T. et al., *Molecular cloning: A laboratory manual* (1982) Cold Spring Harbor Laboratory Press, New York). In general, 10 µg of DNA was digested with 40 units of enzyme. Electrophoresis of DNA digests was carried out in agarose gel (0.8%) in TEB buffer (89 mM Tris, 2 mM EDTA, 89 mM boric acid). DNAs were transferred by Southern capillary blot onto nylon membranes ZETABIND (AMF Cuno, Meriden, Conn.), fixed by UV cross-linking and hybridized to $10^7$ dpm DNA probes labeled by nick translation (Rigby, P. W. J. et al., *J. Mol. Biol.* (1977) 113:237–251) to a specific activity of about $2 \times 10^8$ dpm/µg. Washing was carried out at 65° C. in 2× SSC, 0.2% SDS and subsequently in 0.2× SSC, 0.2% SDS at 65° C.

Isolation of CRIPTO genomic clones.

Genomic clones were isolated from two different human genomic libraries: one obtained by partial MboI digestion of genomic DNA cloned in the BamHI site of the pcos2EMBL Cosmid Vector (Poustka, A. et al., *Proc. Natl. Acad. Sci. USA* (1984), 81:4129–4133), the other obtained by partial MboI digestion of genomic DNA that had been flush ended and cloned into the flush ended XhoI site of Lambda Fix Vector (Stratagene). $5 \times 10^5$ cosmids and $10^6$ phages were screened using the CRIPTO cDNA fragment 2B3 (see FIG. 1C) by standard techniques (Grunstein, M. et al., *Proc. Natl. Acad. Sci. USA* (1975) 72:3961–3965; Benton, W. et al., *Science* (1977) 196:180–182, respectively). The positive clones were analyzed by restriction mapping and the genomic fragments hybridizing to the human cDNA were subcloned in pUC18 Vector (Yanish-Perron, C. et al., *Gene* (1985) 33:103–109) or in pGEM-1 Vector (Promega). DNA sequencing of the genomic subclones was carried out using the modified dideoxynucleotide chain termination procedure (Hattori M. et al., *Nucl. Acids Res*, (1985) 13:7813–7827). An oligonucleotide walking strategy was performed using synthetic 17-mer oligonucleotides (Applied Biosystems) deduced from the genomic sequence previously determined.

S1 nuclease mapping.

Total RNA from undifferentiated teratocarcinoma cells NT2/D1 (Andrews, P. W. et al., *Lab. Invest.* (1984) 50:147–162) was isolated by cell lysis in 4M guanidine thiocyanate and sedimentation through 5.7M CsCl (Chirgwin, J. M. et al., *Biochemistry* (1979) 18:5294–5304). Poly(A)+RNA was selected by chromatography on oligo (dT) cellulose (Aviv, H. et al., *Proc. Natl. Acad. Sci. USA* (1972) 69:1408–1412). 5 µg of poly(A)+RNA or 40 µg of total RNA was hybridized with the 320 bp Sau96 fragment of Cr-1-73-H (FIG. 3), $^{32}$P-5'-end labeled, in 20 µl of 40 mM Pipes, pH 7, 0.4M NaCl, 1 mM EDTA, pH 7, and 80% formamide for 16 h at 50° C. Following hybridization, the reaction was diluted 10-fold with S1 nuclease buffer (0.28M NaCl, 0.05M sodium acetate, pH 4.5, 4.5 mM $ZnSO_4$ and 20 µg/ml single strand DNA). S1 nuclease (1200 units) was added and the reaction mixture was incubated for 2 h at 37° C. The reaction was terminated by the addition of 44 µl of termination buffer (2.5M ammonium acetate and 50 mM EDTA); the DNA:RNA hybrids were extracted with phenol, precipitated with ethanol, resuspended in sequencing dye, heated to 90° C. and resolved on a 6% acrylamide, 7M urea sequencing gel.

Primer extension.

For primer extension analysis, a 35 bp synthetic oligonucleotide, o1 GP2 (3'-CCCGGTAGAAGGACGTCAGGTATCGAAATTGTTAA-5') corresponding to base pairs −9+21 of the first exon was end-labeled using T4 polynucleotide kinase to a specific activity of $10^8$ cpm/µg of poly(A)+mRNA from NT2/D1 cells (Andrews, P. W. et al., *Lab. Invest.* (1984) 50:147–162) in a 40-µl volume containing 10 mM Pipes pH 6.4, 0.4M NaCl, 1 mM EDTA, by heating the reaction mixture for 3 min at 90° C., 2 min at 75° C. and gradual cooling to 42° C. After 14 h at 42° C., the resulting DNA:RNA hybrids were ethanol-precipitated and dissolved in reverse transcription buffer (50 mM Tris HCl pH 8, 0.1M KCl, 10 mM $MgCl_2$) in the presence of 500 µM deoxynucleotides and 20 units of reverse transcriptase. After 1 h at 42° C., the DNA:RNA hybrids were phenol-extracted, ethanol-precipitated, dissolved in sequencing dye, heated to 90° C. and resolved on a 6% acrylamide, 7M urea sequencing gel.

EXAMPLE 1

Genomic complexity of CRIPTO gene-related sequences in human chromosomes

The 2020 bp long CRIPTO cDNA previously described (Ciccodicola, A. et al., *EMBO J.* (1989) 8:1987–1991)

contains an open reading frame of 564 bp, a 245 bp long 5' untranslated region, and a 1209 bp long 3' untranslated region that includes an Alu sequence element.

As a first approach to characterize the genomic organization of the gene encoding the CRIPTO protein, Southern blot analyses were carried out. The two cDNA fragments, 2B3 and G2 (FIG. 1C), used as probes, hybridized to several genomic restriction fragments (FIG. 1A). The 2B3 probe, used to analyze by Southern blot the genomic DNA of mouse and chicken, hybridized to several bands in the lanes containing mouse DNA (FIG. 1B, first three lanes), whereas no hybridization was seen with chicken DNA (FIG. 1B fourth and fifth lanes).

EXAMPLE 2

Isolation and characterization of CRIPTO human genomic clones

To better understand the nature of the CRIPTO gene-related sequences, a human genomic library (Poustka, A. et al., *Proc. Natl. Acad. Sci. USA* (1984), 81:4129–4133) was screened using CRIPTO fragment 2B3 as a probe and 34 positive cosmid clones were isolated. EcoRI restriction analysis of 10 of the isolated clones revealed only 3 different restriction patterns in the inserts.

Figure 3:
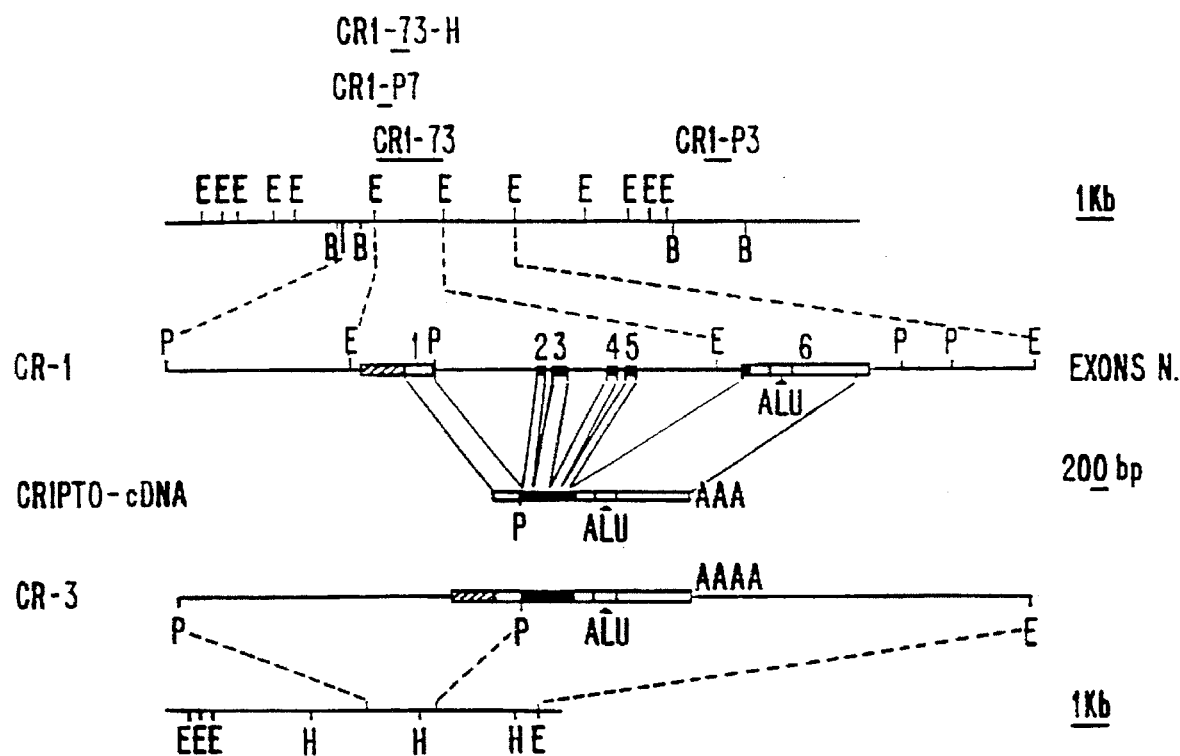
FIG. 3. Maps summarizing information obtained from DNA sequencing and restriction mapping of isolated CRIPTO homologous recombinant clones. Top: Physical map of CR-1. Numbered exons are indicated by black boxes for coding region and white boxes for non-coding regions. The hatched box represents the 440 bp upstream of the most common transcription start present also in CR-3. Restriction sites are indicated: EcoRI (E); BamHI (B); PstI (P). Thick lines above the map denote genomic subclones used as probes. Bottom: Physical map of CR-3. Below are represented the genomic region isolated and EcoRI (E), HindIII (H), PstI (P) restriction sites. CR-3 contains all the exons and a polyA tail (AAAA).

The isolated clones were hybridized to a synthetic oligonucleotide (G1) corresponding to nucleotides –91 to –110 of the 5' non-coding region of CRIPTO cDNA (Ciccodicola, A. et al., *EMBO J.* (1989) 8:1987–1991 and FIGS. 2A–2G), with the intention of isolating the complete gene and discarding possible incomplete pseudogenes. A positive 800 bp PstI/EcoRI fragment (CR-1-P7) was identified in the CR-1 cosmid clone (FIG. 3 top).

DNA sequencing analysis revealed that clone CR-1 includes an intact structural gene encoding the entire human CRIPTO protein. The CRIPTO coding sequence is encoded by six exons spanning a 4.8 kb long DNA interval (FIG. 3 top). The nucleotide sequences at the exon-intron boundaries were established by DNA sequence comparison of cDNA and genomic subclones. The 5' donor and 3' acceptor splice sites in each of the five introns conform to the GT . . . AG rule and agree with the consensus sequence compiled for the exon-intron boundaries (Mount, S. M., *Nucl. Acids Res.*, (1982) 10:459–472) except for the acceptor sequence of the second and third introns (FIG. 2). Exon 1 is 281 bp in length and contains the initiator methionine. The other exons range in size from 52 to 1329 bp. The most 3' exon, 1329 bp in length, contains 118 bp of coding sequence and all of the 3' untranslated region (3' UT), which is 1209 nucleotides long (FIG. 2). The EGF-like domain exhibited by the CRIPTO protein (Ciccedicola et al. 1989) is encoded by exon 4.

A combination of S1 nuclease mapping and primer extension analyses was used to characterize the CR-1 transcription products.

Figure 4A:
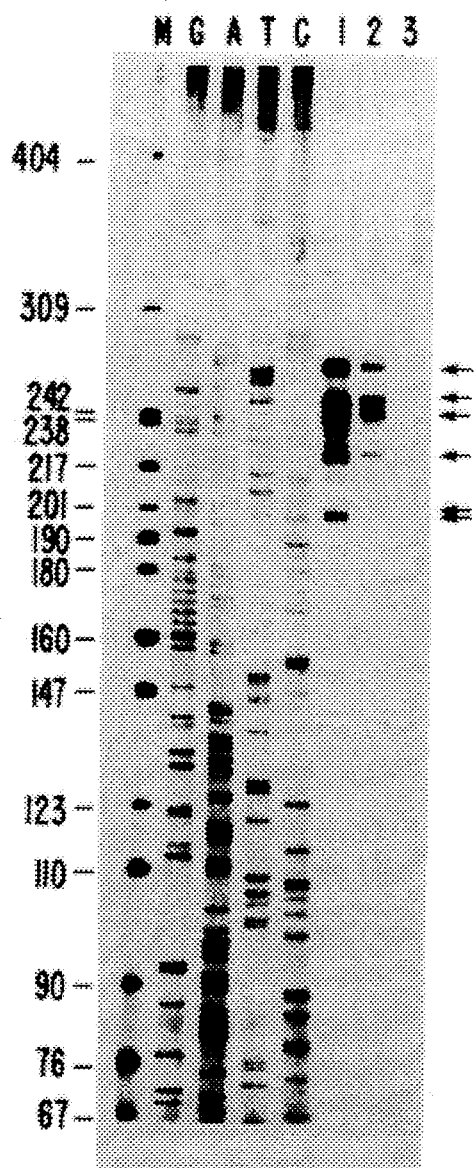
FIGS. 4A, 4B and 4C. S1 nuclease and primer extension analyses.

Since the CRIPTO gene was found to be expressed in an undifferentiated human teratocarcinoma cell line (NT2/D1) (Ciccodicola et al. 1989), poly (A)+RNA isolated from cultured NT2/D1 cells was used. The probe used for S1 nuclease mapping was a double-strand DNA fragment encompassing nucleotides –302 to +18 of the genomic sequence and was labeled with $^{32}$P at the 5' end (FIG. 4C). Five major S1 nuclease-protected fragments (FIG. 4A) mapping between positions –180 to –253 of the genomic sequence were observed (FIG. 4C).

Figure 4B:
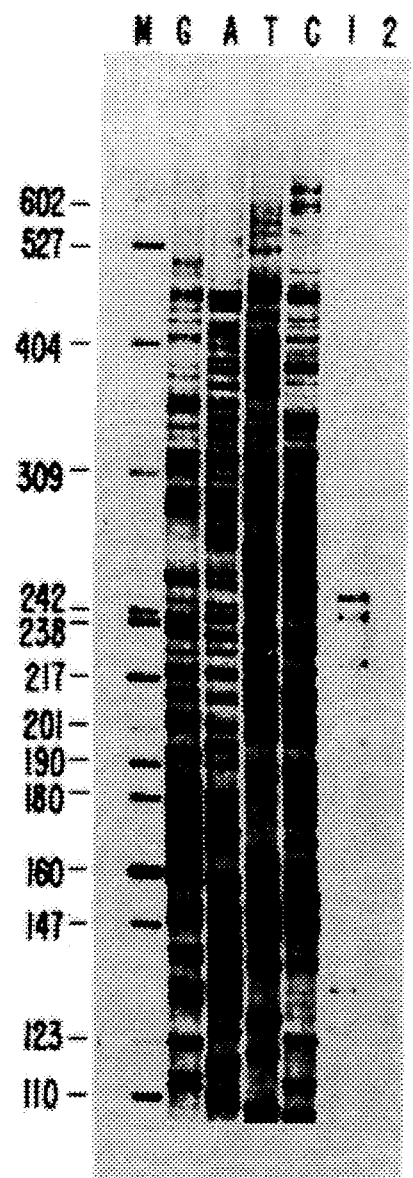
Figure 4C:
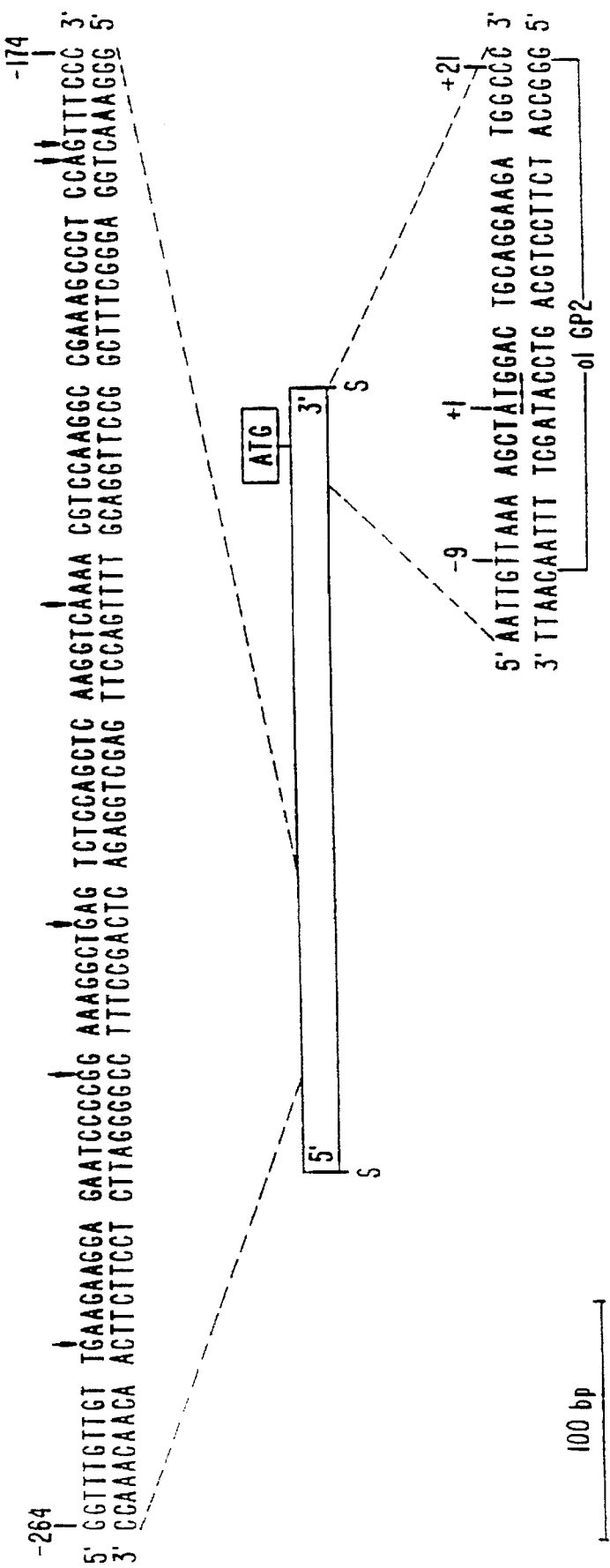

The primer extension assay, performed with ol GP2 (FIG. 4C) confirmed the five major products corresponding in length to the transcripts predicted by S1 analysis (FIG. 4B). It should be noted that other bands are seen in primer extension experiments probably due to both minor RNA species and early termination of the reverse transcriptase reaction.

EXAMPLE 3

Chromosome mapping with somatic cell hybrid panel

A chromosome mapping panel was used to assign the CR-1 gene to human chromosomes. A 1.5 kb long PstI fragment derived from CR-1 (CR-1-P3, FIG. 3 top) was used to probe a Southern blot of TaqI-digested genomic DNAs prepared from 23 hamster human somatic cell hybrids (Table I). Under conditions of high stringency one human specific genomic fragment of 4.5 kb hybridized to the probe. The presence of the 4.5 kb fragment could be clearly distinguished in the DNA of the hybrid cell lines containing chromosome 3 (Table I).

Figures 5A, 5B:
FIGS. 5A and 5B. Southern blot analysis using the CR-1-P7 probe.

When the EcoRI-PstI fragment (CR-1-P7) containing 800 bp upstream of the translation initiation (see FIG. 3 top) was used to probe the same Southern blot described previously and shown in FIGS. 1A and 1B, hybridization to two fragments was seen (e.g., in the lane containing human DNA digested with EcoRI and PstI (FIG. 5A), the 0.8 kb band corresponds to the genomic sequence CR-1). This indicated that the 5' region of the CR-1 gene was present in two copies in the human genome. When the CR-1-P7 fragment was used to probe the above-mentioned hamster-human somatic cell hybrid panel, it was possible to obtain the segregation of the two sequences (FIG. 5B). Because of the hybridization pattern summarized in Table I and, in particular, the pattern obtained using the hybrid cell lines containing portions of the X chromosome already described (Rocchi et al. 1986), the second genomic copy can be assigned to the Xq21-22 region.

TABLE I

| Segregation of CRIPTO-related sequences in human/hamster hybrids | | | |
| --- | --- | --- | --- |
| Cell lines | Chromosomes present | CR-1 | CR-3 |
| HY.19.16T3D | Xq–, 10, 12, 13, 14, 15, 18, 20 | – | – |
| HY.22AZA1 | t(X;X)[a], 5, 12, 14, 17, 18, 19 | – | + |
| HY.31.24E | X, 5, 8, 11, 12, 14, 21 | – | + |
| HY.36.1 | X, 8, 11, 19 | – | + |
| HY.60A | X, 5, 6, 8, 13, 14, 18, 20 | – | + |
| HY.7081A | t(X;21)[b], 6, 15, 16 | – | – |
| HY.7082 | t(X;21)[b], 6, 13, 15, 16 | – | – |
| HY.75E1 | X, 5, 9, 12 | – | + |

TABLE I-continued

Segregation of CRIPTO-related sequences in human/hamster hybrids

| Cell lines | Chromosomes present | CR-1 | CR-3 |
|---|---|---|---|
| HY.94A | X, 6, 7, 8, 16, 22 | − | + |
| HY.94BT1 | t(X;Y)[c], 4, 7, 9, 11, 12, 20 | − | + |
| HY.95A1 | X, 3, 5, 10, 11, 14 | + | + |
| HY.95B | X, 4, 6, 7, 14, 18, 22 | − | + |
| HY.95S | X, 2, 3, 13, 21 | + | + |
| HY.112F7 | t(X;11)[d], 3, 4, 8, 10, 20 | + | + |
| RJ.369.1T2 | 13, 22 | − | − |
| Y.173.5CT3 | Xi, 1, 3, 4, 6, 8, 11, 12, 14, 15, 18, 21, 22 | + | + |
| YC2T1 | X, 1, 11, 12, 14, 18, 19, 20 | − | + |
| HY.136C | X | − | + |
| Y.X6.8B2 | t(X;6)[e], 1, 3, 5, 12, 13, 14, 15, 17, 21, 22 | + | + |
| Y.162AZA | t(X;hamster)[f] | − | + |
| HY.87Z4 | t(X;11)[g], 1, 2, 4, 5, 6, 12, 15, 20 | − | − |
| HY.85D30T2 | t(X;1)[h], 2, 3, 8, 11, 13, 18, 21 | + | + |
| HY.84T2 | Y | − | − |
| Chromosome assignment | | 3 | Xq21–Xq22 |
| Number concordant + | | 6 | 17 |
| Number concordant − | | 17 | 6 |
| Number discordant | | 0 | 0 |

Note: + and − indicate, respectively, presence or absence of CR-1 and CR-3 sequences
[a]Xqter −>Xq21::Xp22.3 −>Xqter
[b]Xqter −>Xq21::21p13 −>21qter
[c]Xqter −>Xq22.3::Yp −>Yqter
[d]Xqter −>Xq11.1::11p11.2 −>11q11
[e]Xqter −>Xq21.3::6q27 −>6pter
[f]Xpter −>Xq27.3::hamster
[g]Xqter −>Xq26::11q23 −>11pter

EXAMPLE 4

Isolation and characterization of a second genomic CRIPTO-related sequence

A genomic library was screened to isolate the genomic clones containing the 5' cDNA non-coding region using as probe the labeled CR-1-P7 DNA fragment (FIG. 3). Only two different classes of recombinant phages were found exhibiting the restriction pattern expected from the Southern blot (FIG. 5A and 5B).

The restriction map of clone CR-3 is shown in FIG. 3 bottom. To investigate whether the CRIPTO related genomic sequences from recombinant lambda CR-3 clones encode a complete CRIPTO protein, the nucleotide sequence of a 2688 bp fragment hybridizing to 2B3 and G2 was determined and compared this sequence with that of cDNA (FIGS. 2A–2G and 3 bottom).

Analysis of the nucleotide sequence of CR-3 revealed that this clone includes a complete CRIPTO cDNA lacking introns and containing a poly(A) tract at the 3' end. Seven single base pair substitutions are observed in the coding region (FIGS. 2A–2G) and six of these give rise to amino acid changes. The 3' non-coding sequence is less similar (97% identical) to CR-1. Most of the base changes, deletions and insertions fall within the inverted Alu sequence. The unusual polyA addition site AGTAAA present in the CR-1 gene is conserved also in CR-3. The similarity between CR-1 and CR-3 extends for 697 nucleotides upstream of the initiator AUG where it is possible to observe 7 base pair substitutions and 6 nucleotide deletions.

All publications mentioned hereinabove are hereby incorporated in their entirety by reference.

While the foregoing invention has been described in some detail for purposes of clarity and understanding, it will be appreciated by one skilled in the art from a reading of this disclosure that various changes in form and detail can be made without departing from the true scope of the invention and appended claims.

---

What is claimed is:

1. A method of measuring an amount of CR-3 in a sample, comprising:
    a) contacting said sample with non-cross reactive antibodies having binding affinity to a human CRIPTO-related gene (CR-3) product, but not to CR-1, under conditions such that immunocomplexes form, and
    b) measuring an amount of immunocomplexes formed between said antibodies and any CR-3 in said sample.

2. A method of measuring an amount of CR-3 in a sample, comprising:
    a) contacting said sample with non-cross reactive antibodies having binding affinity to a human CRIPTO-related gene (CR-3) product having an amino acid sequence set forth in SEQ ID NO:5, under conditions such that immunocomplexes form, and
    b) measuring an amount of immunocomplexes formed between said antibodies and any CR-3 in said sample.

3. The method of claim 1, wherein said antibodies are monoclonal.

4. The method of claim 1, wherein said antibodies are polyclonal.

5. The method of claim 2, wherein said antibodies are monoclonal.

6. The method of claim 2, wherein said antibodies are polyclonal.

* * * * *